US010086070B2

(12) United States Patent
Lewis

(10) Patent No.: US 10,086,070 B2
(45) Date of Patent: Oct. 2, 2018

(54) COMBINED THERAPY OF ALPHA-1-ANTITRYPSIN AND TEMPORAL T-CELL DEPLETION FOR PREVENTING GRAFT REJECTION

(71) Applicant: BEN GURION UNIVERSITY OF THE NEGEV RESEARCH AND DEVELOPMENT AUTHORITY, Beer Sheva (IL)

(72) Inventor: Eli Lewis, Beer Sheva (IL)

(73) Assignee: Ben Gurion University of the Neger Research and Development Authority, Beer Sheva (IL)

( * ) Notice: Subject to any disclaimer, the term of this patent is extended or adjusted under 35 U.S.C. 154(b) by 0 days.

(21) Appl. No.: 15/477,379

(22) Filed: Apr. 3, 2017

(65) Prior Publication Data

US 2017/0202961 A1 Jul. 20, 2017

Related U.S. Application Data

(63) Continuation of application No. 14/380,118, filed as application No. PCT/IB2013/051562 on Feb. 27, 2013.

(60) Provisional application No. 61/603,970, filed on Feb. 28, 2012.

(51) Int. Cl.
| | |
|---|---|
| *A61K 38/57* | (2006.01) |
| *A61K 39/395* | (2006.01) |
| *A61K 35/39* | (2015.01) |
| *A61K 38/14* | (2006.01) |
| *A61K 38/19* | (2006.01) |
| *A61K 38/21* | (2006.01) |
| *C07K 16/40* | (2006.01) |
| *A61K 39/00* | (2006.01) |

(52) U.S. Cl.
CPC .......... *A61K 39/395* (2013.01); *A61K 35/39* (2013.01); *A61K 38/14* (2013.01); *A61K 38/191* (2013.01); *A61K 38/217* (2013.01); *A61K 38/57* (2013.01); *A61K 39/3955* (2013.01); *A61K 39/39541* (2013.01); *C07K 16/40* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 2009/0118162 A1 | 5/2009 | Shapiro et al. | |
| 2009/0220518 A1 | 9/2009 | Dinarello et al. | |
| 2010/0167259 A1* | 7/2010 | Matsumoto | A01N 1/0252 435/1.1 |

FOREIGN PATENT DOCUMENTS

| | | |
|---|---|---|
| WO | 2006133403 A2 | 12/2006 |
| WO | 2008138017 | 11/2008 |
| WO | 2009046015 | 4/2009 |

OTHER PUBLICATIONS

Breimer, Xenotransplantation 2011: 18: 215-228. (Year: 2011).*
Loganathan et al., Transplantation 2011;92: 1222-1230. (Year: 2011).*
Matsuda et al., Fulminant liver failure triggered by therapeutic antibody treatment in a mouse model, International Journal of Oncology 29: 1119-1125, 2006 (7 pages).
Fischer A., The use of monoclonal antibodies in allogeneic bone marrow transplantation. British Journal of Haematology. vol. 83, Issue 4, pp. 531-534, Apr. 1993 (4 pages).
James Ferrara Kenneth R. Cooke H. Joachim Deeg Sep. 13, 1996. Graff-vs.-Host Disease, Second Edition: CRC Press, p. 409 (3 pages).
Bumgardner et al. "Patterns of Immune Responses Evoked by Allogenic Hepatocytes", Transplantation, vol. 68, Aug. 27, 1999, pp. 555-562.
Tchorsh-Yutsis et al., "Embryonic Pig Pancreatic Tissue for the Treatment of Diabetes: Potential Role of Immune Suppression with off-the-shelf Third Party Regulatory T Cells", Transplantation, Williams and Williams, GB, vol. 91, No. 4, Feb. 1, 2011, pp. 398-405.
Koulmanda et al., "Prolonged survival of fetal pig islet xenografts in mice lacking the capacity for an indirect response", Xenotransplantation, vol. 11, No. 6, Nov. 1, 2004, pp. 525-530.
Fox et al., "Innate immunity and graft rejection", Immunological Reviews, vol. 173, No. 1, Feb. 1, 2000, pp. 141-147.
Koulmanda et al., "Curative and beta cell regenerative effects of alpha I-antitrypsin treatment in autoimmune diabetic NOD mice", Proc Natl Acad Sci USA, 2008, pp. 16242-16247.
Arefanian et al., "Combination of anti-CD4 with anti-LFA-1 and anti-CD154 monoclonal antibodies promotes long-term survival and function of neonatal porcine islet xenografts in spontaneously diabetic NOD mice", Cell Transplantation, vol. 16, pp. 787-798, 2007.
Arefanian et al., "Short-term administrations of a combination of anti-LFA-1 and anti-CD154 monoclonal antibodies induce tolerance to neonatal porcine islet xenografts in mice", Diabetes, vol. 59, pp. 958-966, Apr. 2010.
Tchorsh-Yutsis et al., "Pig Embryonic Pancreatic Tissue as a Source for Transplantation in Diabetes", Diabetes, vol. 58, pp. 1585-1594, Jul. 2009.
Shahaf et al., "α-1-Antitrypsin Gene Delivery Reduces Inflammation, Increases T-Regulatory Cell Population Size and Prevents Islet Allograft Rejection", Mol Med 17 (9-10), pp. 1000-1011, 2011.
Lewis et al., "α1-Antitrypsin monotherapy prolongs islet allograft survival in mice", PNAS, vol. 102, No. 34, pp. 12153-12158, Aug. 23, 2005.
Lewis et al.,"α1-Antitrypsin monotherapy induces immune tolerance during islet allograft transplantation in mice", PNAS, vol. 105, No. 42, pp. 16236-16241. Oct. 21, 2008.
International Search Report of PCT Application No. PCT/IB213/051562, dated Jul. 8, 2013, 14 pages.

(Continued)

*Primary Examiner* — Zachary S Skelding
(74) *Attorney, Agent, or Firm* — Roach Brown McCarthy & Gruber, P.C.; Kevin D. McCarthy

(57) ABSTRACT

A method of preventing or treating xenotransplant rejection in a subject in need thereof is disclosed. The method comprises administering a therapeutically effective amount of alpha-1-antitrypsin (AAT) in combination with a therapeutically effective amount of an anti-CD8 antibody or an antigen binding fragment thereof.

12 Claims, 6 Drawing Sheets

Specification includes a Sequence Listing.

(56) References Cited

OTHER PUBLICATIONS

Supplementary European Search Report of corresponding European application No. 13755285, dated Oct. 9, 2015, 13 pages.
Odgen et al. Mean Body Weight, Height, and Body Mass Index, United States 1960-2002 Advance Data, No. 347, Oct. 27, 2004 (18 pages).
Baron et al. Cutting Edge Communication, Nonmyeloablative Stem Cell Transplantation with CD8-Depleted or CD34-Selected Peripheral Blood Stem Cells, Journal of Hematotherapy and Stem Cell Research 11:301-314 (2002) (14 pages).
Bumgardner et al. (Transplantation, vol. 68(4), Aug. 27, 1999, pp. 555-562) 9 pages.
Strom et al. (Therapeutic Immunology edited by Austen et al., Blackwell Science, Cambridge, MA 1996, pp. 451-456 (6 pages).
Summary of Safety and Effectiveness, Isolex 300 and 300i Magnetic cell Selection System, pp. 1-31, 1999 (31 pages).
Nimer et al (Transplation, vol. 57, 82-87, No. 1 1994) (7 pages).
Snyder et al. (Bllod 2007; 109:5399-5406) (9 pages).
Baron et al. T-cell reconstitution after unmanipulated, CD8-depleted or CD34-selected nonmyeloablative peripheral blood stem-cell transplantation (Transplantaton vol. 76, 1705-13 (2003) (9 pages).
Mouquet et al. The presense of apoptotic bone marrow cells impairs the efficacy of cardiac cell therapy, Cell Transplantation, vol. 20, pp. 1087-1097 (2011) (12 pages).

\* cited by examiner

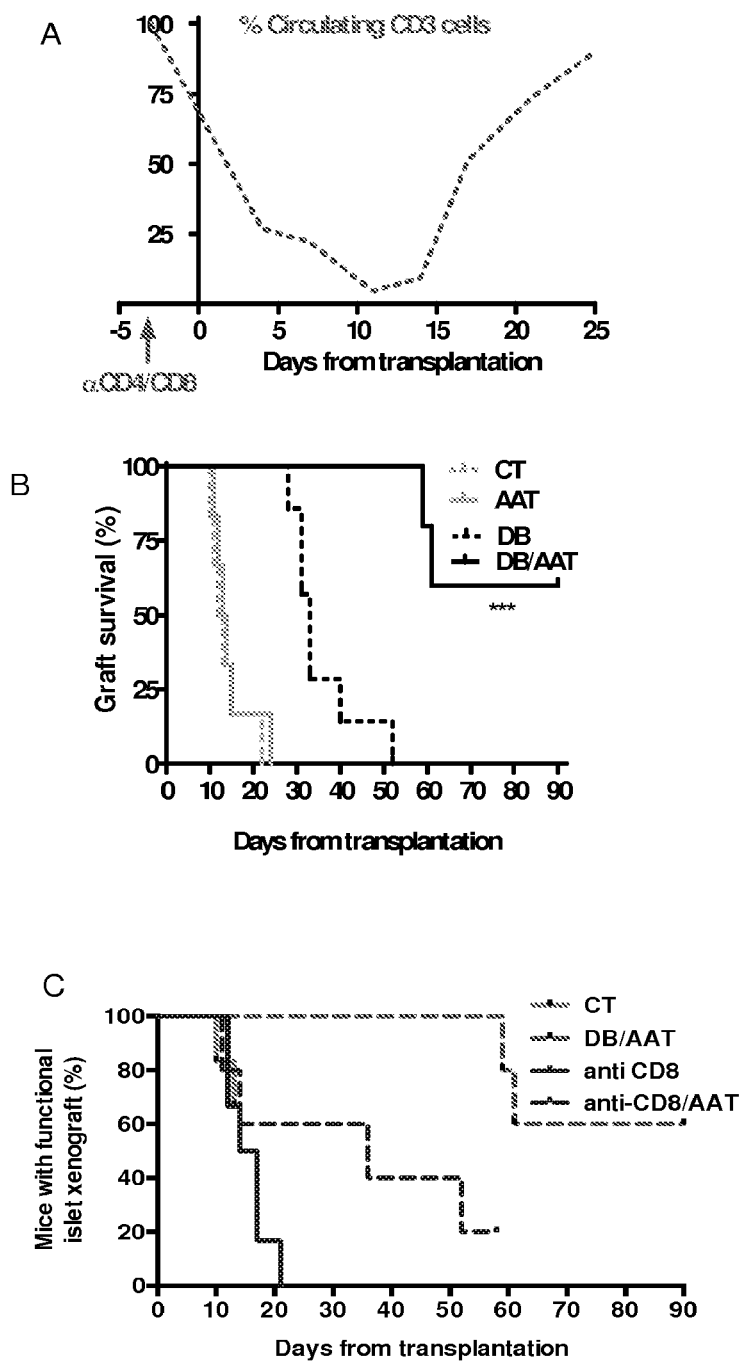

Figure 3 Continue
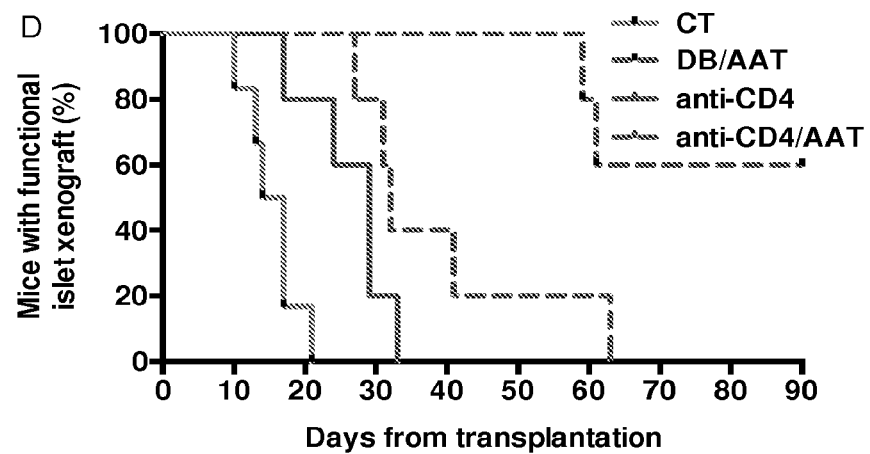
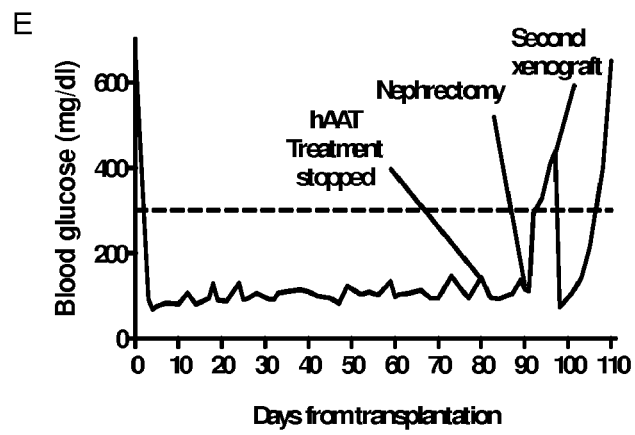

COMBINED THERAPY OF ALPHA-1-ANTITRYPSIN AND TEMPORAL T-CELL DEPLETION FOR PREVENTING GRAFT REJECTION

FIELD OF THE INVENTION

The present invention relates to compositions and methods for the prevention and treatment of graft rejection, including xenograft rejection, and for attenuating host responses in transplantation of cells, pancreatic islets, tissues and organs. More specifically, the compositions and methods of the present invention relate to combined therapies comprising treatment of alpha-1-antitrypsin and temporary T-cell depletion in the graft recipient.

BACKGROUND OF THE INVENTION

Transplantation systems such as organ transplantations have become important, effective and at times the sole therapies for many life-threatening end-stage diseases.

However, injurious immune responses are still the major barrier for successful transplantation. This is manifested in irreversible and life-threatening graft failure (host-versus-graft response, or HVG) or pathological immune reactivity of bone-marrow transplants graft-versus-host disease (GVHD). Importantly, current immunosuppression holds severe side-effect that limit the possibility of dose increment.

Pancreatic islet transplantation can provide type-1 diabetes patients with functional islets and physiological circulating glucose levels. However, shortage of human donors represents a critical obstacle. Islet xenograft transplantation from non-human donors provides an alternative for human islet allotransplantation; in addition to providing an array of islet sources, xenografts offer the advantage of elective procedures (that is, the donor is recruited upon availability rather than the patient), and potentially manipulating donor cells towards superior islet function. However, the xenoimmune response is exceptionally rigorous, and the side effects encountered with use of current immunosuppression outweighs the benefit of the procedure.

The immunological mechanism of xenograft rejection is distinct to allograft. Xenograft rejection is largely attributed to vast antigen disparity between species, thus triggering multiple arms of the immune response. Indeed, in addition to host $CD4^+$ T cell involvement, evidence suggests that $CD8^+$ T cells and B cells partake in xenograft rejection. Additionally, inflammation limits islet xenograft survival, particularly in early days post-transplantation, a challenging therapeutic obstacle considering that diabetogenic corticosteroids are excluded from current islet transplantation protocols. Within this context, the desired emergence of protective regulatory T cells (Tregs) appears further intangible.

Experimentally, xenograft survival prolongation has been achieved by several routes, most of which may not easily translate to human use. Of these, approaches that deplete immune cells have been experimentally successful and have entered human use. Anti-thymocyte-globulin (ATG), a regimen comprised of polyclonal antibodies that temporarily deplete T cells, is currently used for prevention of acute rejection in organ transplantation. Combination of anti-CD4 and anti-CD8 antibodies in mice (referred to as T cell debulking therapy) may represent the use of ATG in patients, as it achieves a similar temporary decline in T-cell numbers (Tchorsh-Yutsis et al. Transplantation 2011; 91(4):398-405; Tchorsh-Yutsis et al. Diabetes 2009; 58(7):1585-1594). Temporal T cell depletion delays clonal T cell activation in the associated draining lymph nodes (DLN) and allows grafted islets to evade T cell-mediated destruction in the first ~2 weeks post-transplantation. Indeed, anti-CD8 and anti-CD4 antibodies extend islet xenograft survival, albeit not indefinitely (Koulmanda et al. Xenotransplantation 2004; 11(6):525-530).

Human α1-antitrypsin (hAAT), a readily available plasma-derived protein with potent anti-inflammatory and tissue-protective activities, promotes islet all ograft survival and induces strain-specific immune tolerance in the absence of a direct effect on T-cell responses (Shahaf et al., Mol Med. 2011 September-October; 17(9-10): 1000-1011; Lewis et al., Proc Natl Acad Sci USA 2008; 105(42):16236-16241; and Lewis et al., Proc Natl Acad Sci USA 2005; 102(34):12153-12158). hAAT also targets anti-islet autoimmune responses in animals (Koulmanda et al., Proc Natl Acad Sci USA 2008; 105(42):16242-16247). The cellular targets of hAAT include non-T cells such as dendritic cells, B lymphocytes, macrophages and neutrophils, resulting in reduced levels and activity of inflammatory mediators such as IL-1β, tumor necrosis factor (TNF) α, monocyte chemotactic protein (MCP)-1 and nitric oxide, as well as elevating levels of IL-10 and IL-1 receptor antagonist. hAAT has been shown to directly protect islets from inflammatory injury, apoptosis and isolation-related damage.

US Pat. Appl. No. 20090118162, to an inventor of the current invention and co-workers, relates to compositions and methods for inhibition of graft rejection and promotion of graft survival.

US Pat. Appl. No. 20090220518, to an inventor of the current invention and co-workers, relates to treating, reducing or preventing transplantation rejection and/or side effects associated with transplantation.

Nowhere in the background art is it taught or suggested that xenograft rejection may be prevented by combination therapy comprising AAT and temporary T cell depletion, particularly, anti-CD4 and anti-CD8 antibodies administration.

There remains an unmet medical need for providing methods for preventing and treating xenograft rejection, and for attenuating host responses in transplantation of tissues, organs or cells.

SUMMARY OF THE INVENTION

The present invention provides compositions and methods for the prevention and treatment of xenograft rejection, and for attenuating host responses in xenotransplantation of tissues, organs and cells. More specifically, the present invention provides compositions and methods of combined therapies comprising treatment of alpha-1-antitrypsin (AAT) and temporary T-cell depletion in the graft recipient.

It is now disclosed, for the first time, that islet xenotransplant survival is remarkably extended by a combination therapy of AAT treatment and temporary T cell depletion. As exemplified herein below, xenograft recipients were treated separately with AAT or T cell depletion, however, this resulted in acute rejection, or delayed-onset acute rejection of the graft, respectively. Further, combination therapy of AAT with co-stimulation blockade using anti-CD154/LFA-1 antibodies did not result in significant change in xenotransplant rejection. Surprisingly, co-administration of AAT and T cell depletion using anti-CD4 and anti-CD8 antibodies resulted in prolonging xenograft survival.

According to one aspect, the present invention provides a method of preventing or treating xenotransplant rejection in a subject in need thereof, the method comprises administering to said subject a therapeutically effective amount of AAT in combination with a therapeutically effective amount of at least one temporary T cell depleting agent.

According to exemplary embodiments, the at least one temporary T cell depleting agent is selected from anti-CD4 and anti-CD8 antibodies, or an antigen binding fragment thereof. According to another embodiment, the at least one temporary T cell depleting agent is an anti-CD4 antibody, or an antigen binding fragments thereof. According to another embodiment, the at least one temporary T cell depleting agent is an anti-CD8 antibody, or an antigen binding fragment thereof. According to another embodiment, the at least one temporary T cell depleting agent is anti-CD4 and anti-CD8 antibodies, or antigen binding fragments thereof.

According to another embodiment, the at least one temporary T cell depleting agent is selected from the group consisting of anti-CD3, anti-CD4, anti-CD25, anti-CD8a, anti-TCR, anti-TCR-gamma-delta and anti-thymocyteglobulin (ATG), or an antigen binding fragment thereof. Each possibility is a separate embodiment of the present invention.

According to some embodiments, the temporary T cell depleting agent is administered prior to transplantation. According to another embodiment, said temporary T cell depleting agent is administered no more than 14 days prior to transplantation. According to another embodiment, said temporary T cell depleting agent is administered no more than 3 days prior to transplantation. According to another embodiment, said temporary T cell depleting agent administration is concomitant.

According to another embodiment, the AAT is human AAT (hAAT). According to another embodiment, said hAAT comprises an amino acid sequence as set forth in SEQ ID NO: 1. According to another embodiment, said hAAT consists of an amino acid sequence as set forth in SEQ ID NO: 1. According to another embodiment, said AAT is recombinant hAAT. According to another embodiment, said AAT is an analog, derivative or fragment of hAAT.

According to another embodiment, AAT administration is a long term administration. According to another embodiment, said AAT administration is sequential. According to another embodiment, said AAT administered is a single-dose administration. According to another embodiment, AAT is administered prior to transplantation, following transplantation or a combination thereof. According to another embodiment, administering AAT prior to treatment is for no more than 10 days prior to transplantation.

According to another embodiment, the subject is a human. According to another embodiment, the xenotransplant is from a nonhuman mammal. According to another embodiment, the nonhuman mammal is a nonhuman primate. According to a particular embodiment, the nonhuman mammal is selected from the group consisting of a pig, dog or cow. According to yet another particular embodiment, the nonhuman mammal is a pig. According to the methods of the invention the graft is genetically modified.

According to another embodiment, said xenotransplant is selected from the group consisting of pancreatic islet cells, pancreas, heart, lung, kidney, liver or skin. According to another embodiment, the xenotransplant is pancreatic islet cells. According to another embodiment, the xenotransplant is skin.

According to another aspect, the present invention provides a method of preventing or treating graft rejection in a subject afflicted with graft dysfunction, the method comprises administering to the recipient a therapeutically effective amount of AAT in combination with a therapeutically effective amount of a temporary T cell depleting agent.

According to another embodiment, said graft is selected from the group consisting of pancreatic islet cells, hematopoietic cells, stem cells, pancreas, heart, lung, kidney, liver or skin. According to another embodiment, the graft is pancreatic islet cells. According to another embodiment, the graft is hematopoietic cell. According to some embodiments, said graft is a xenograft. Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3 depicts graft survival following AAT treatment combined with debulking therapy. Rat islets were grafted into mice that were treated with anti-CD4/CD8 depleting antibodies, in the absence of AAT therapy (n=7) or with added AAT therapy (n=5). (A) $CD45^+CD3^+$ cells from peripheral blood, as monitored by FACS analysis. Results presented as the percent out of initial amount prior to injection. Representative follow-up out of 10 mice. (B) Islet xenograft survival curve. ***$p<0.001$ between DB and BD/AAT. (C) The percentage of mice having functional islet xenograft following CT, DB/AAT, anti-CD8, and anti-CD8/AAT treatments. (D) The percentage of mice having functional islet xenograft following CT, DB/AAT, anti-CD4, and anti-CD4/AAT treatments. (E) Glucose follow-up. Representative mouse. Milestones indicated: hAAT treatment stopped, therapy withdrawn followed by glucose follow-up; nephrectomy, graft explantation followed by glucose follow-up; second xenograft, rat islets grafted into the right renal subcapsular space followed by glucose follow-up. FIG. 1D, are shown over gray background, next to day 90 explants from mice treated by the combination of debulking therapy and AAT (DB/AAT). Results expressed as fold change from CT, mean±SEM from n=3/group; **$p<0.01$.

DETAILED DESCRIPTION OF THE INVENTION

Figure 1:
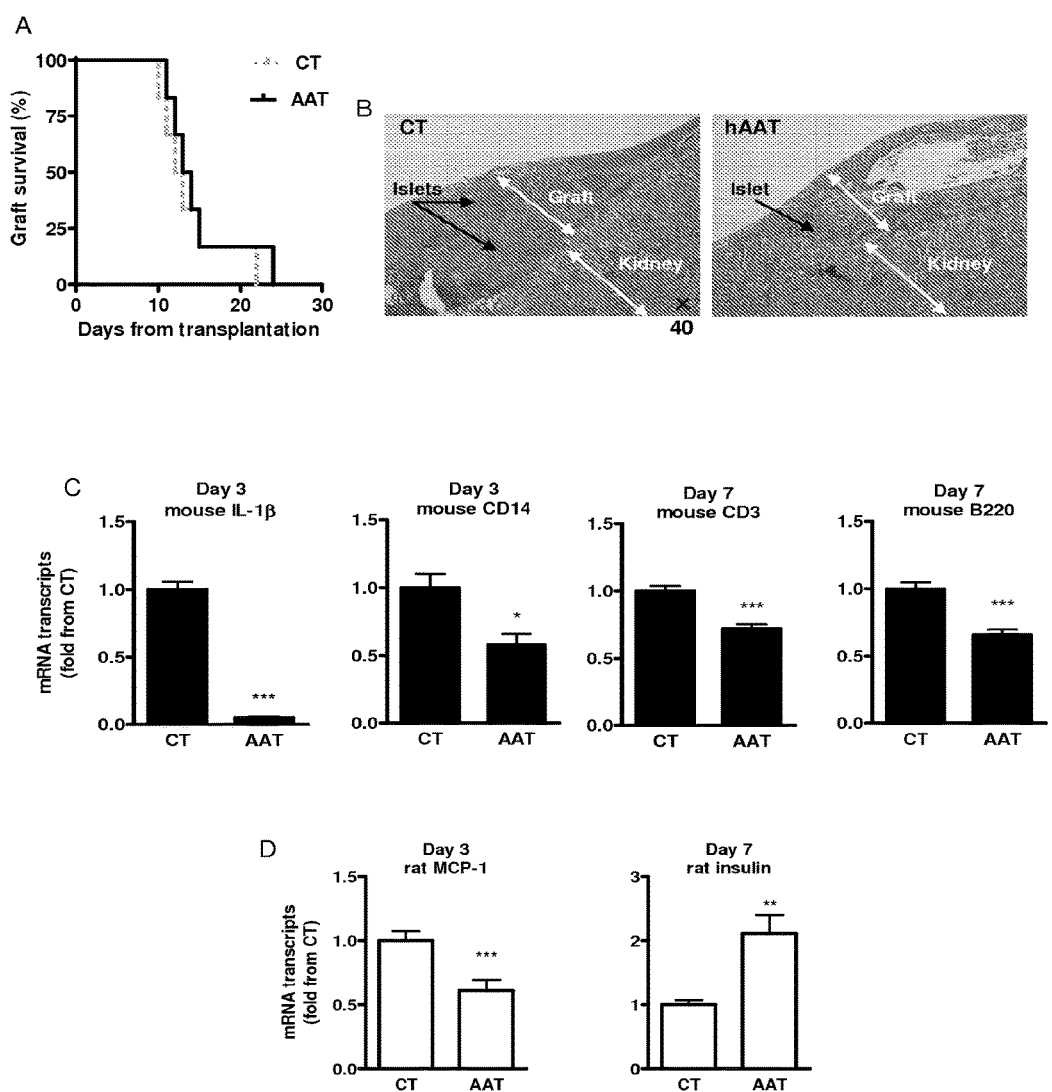
FIG. 1 depicts human AAT monotherapy during pancreatic islet xenotransplantation. Rat pancreatic islets were grafted into the renal subcapsular space of hyperglycemic mice. Recipients were treated with saline (CT) or human AAT throughout the experiment. (A) Islet graft survival curve (n=6/group). (B) Graft histology. Representative day-seven explanted grafts from CT and hATT-monotreated mice (n=3/group). Black arrows, remains of rat pancreatic islets. (C) Mouse gene expression at graft site. Grafts were explanted at indicated times after transplantation. Mean±SEM from n=3 grafts/group; *$p<0.05$, $p<0.01$, *$p<0.001$. (D) Rat gene expression at graft site. Grafts were explanted at indicated times after transplantation. Mean±SEM from n=3 grafts/group; **$p<0.01$.

The invention is directed to compositions and methods for the prevention and treatment of xenograft rejection, and for attenuating host immune responses following xenograft transplantation of tissues, organs and cells. Further, the present invention provides compositions and methods for suppressing the immune response of a graft recipient non-responsive or resistant to a first line treatment, including, but not limited to subjects afflicted with graft dysfunction.

Human AAT (hAAT) monotherapy has been recently shown to protect islet allografts from acute rejection and facilitates strain-specific immune tolerance, however, hAAT monotherapy appears insufficient to allow xenograft acceptance. As demonstrated herein below, AAT monotherapy resulted in xenografts rejection despite attempts to prolong the treatment and/or extend its time course. Considering that xenograft rejection is difficult to control, this would seem the final option for involvement of AAT in this context. In addition, an attempt to combine AAT therapy with co-stimulation blockade using anti-CD154/LFA-1 did not result in significant change in xenotransplant rejection as well. Unexpectedly, prevention of xenograft rejection was achieved using a combination therapy of AAT and temporary T cell depletion using anti-CD4/CD8 antibodies.

Administration of AAT and anti-CD4 and anti-CD8 antibodies to xenograft recipients resulted in a synergistic effect of prolonging islet xenograft survival. Since AAT does not directly inhibit T cell responses, these findings indicate that AAT directs the immune response in the first stages post-transplantation in a manner that is compromised by the presence of uninterrupted activated T cells. Therefore, without wishing to be bound by any particular theory or mechanism of action, the temporary elimination of T cells together with hAAT, affords xenografts improved conditions for recovery and survival, and provides the re-emerging T cells with less danger signals.

In some embodiments the present invention provides a pharmaceutical composition comprising a therapeutically effective amount of AAT and a therapeutically effective amount of at least one temporary T cell depleting agent, including but not limited to, anti-CD4 and/or anti-CD8 antibodies. In some embodiments the present invention provides synergistic compositions of AAT and at least one temporary T cell depleting agent for use in the prevention and treatment of xenograft rejection. In another embodiment, the present invention provides synergistic compositions of AAT and at least one temporary T cell depleting agent for use in preventing or treating graft rejection in a subject non-responsive or resistant to a first-line immunosuppressive treatment. In additional embodiments, the present invention provides synergistic compositions of AAT and at least one temporary T cell depleting agent for use in preventing or treating graft rejection in a subject initially afflicted with graft dysfunction.

The term "initially afflicted with graft dysfunction" refers to the earliest point of detection of an ongoing graft's failure. A subject afflicted with graft dysfunction is, in some embodiment, a graft recipient non-responsive to first-line immunosuppressive protocol or, in additional embodiments, any subsequent immunosuppressive treatment. In specific embodiments, said subject is a treatment-resistant subject.

Typically, in order to minimize the probability of graft rejection, graft recipients undergo immunosuppressive therapy before, during and after transplantation. In specific embodiments, said first-line immunosuppressive treatment is steroid treatment, including but not limited to corticosteroids. Corticosteroid therapy is typically administered at a high dose at the time of transplantation and then gradually reduced to a maintenance dose, which is given indefinitely. The approach ablates immune responses, but does not alter the profile of the immune cells that recover from the effects of steroids. In additional embodiments, said first-line immunosuppressive treatment is selected from the group consisting of: calcineurin inhibitors (CNIs), cyclosporine, tacrolimus, purine metabolism inhibitors, azathioprine, mycophenolate mofetil, rapamycins, sirolimus, everolimus and immunosuppressive immunoglobulin (including anti-lymphocyte globulin (ALG) and antithymocyte globulin (ATG)). Each possibility is a separate embodiment of the invention.

In some embodiments, the methods of the present invention are useful for preventing or treating the rejection of an organ transplant and/or a non-organ transplant. For example lung, kidney, heart, liver, cornea, skin, bone marrow, pancreatic islet, pancreas transplant or combinations thereof are contemplated. In some embodiments, the methods of the present invention are useful for preventing or treating the rejection of transplanted cells, tissues or organs selected from hematopoietic cells, stem cells, pancreatic islet cells, heart, lung, kidney, liver, skin and other cells, organs or tissues transplanted from donor to recipient.

In specific embodiments, the transplanted cells are genetically modified cells. The term "genetically modified cells" as referred to herein relates to cells being transfected by a vector, as exemplified by an expression vector comprising the coding sequence of a gene of interest, said cells capable of expressing said gene. Methods for genetically modifying cells, such as hematopoietic cells, stem cells or pancreatic islet cells are well known in the art.

The phrase "therapeutically effective amounts" is intended to qualify the amount of each agent for use in the combination therapy which will achieve the goal of improvement in severity and the frequency of incidence over treatment of each agent by itself, while avoiding adverse side effects typically associated with alternative therapies. In specific embodiments, the therapeutically effective amount of at least one agent of the invention (AAT or T cell depleting agent) is lower than the amount used in monotherapy using said agent. In yet another embodiment, the therapeutically effective amount of AAT is lower than the amount used in monotherapy using said agent.

According to some embodiments, AAT is administered at a dose of 5-300 mg/kg. According to some embodiments, AAT is administered at a dose of 10-280 mg/kg. According to some embodiments, AAT is administered at a dose of 15-260 mg/kg. According to another embodiment, AAT is administered at a dose of 45-240 mg/kg.

According to some embodiments, the T cell depleting agent is an antibody or antigen binding fragment thereof, and is administered at a dose effective for temporarily depleting T cell. Typically, antibodies are administered at a dose of 0.1-20 mg/kg. According to some embodiments, said T cell depleting antibody is administered at a dose of 0.5-10 mg/kg.

The phrase "combination therapy" in defining the use of AAT in combination with at least one T cell depleting agent, is intended to embrace administration of each agent in a distinct manner in a regimen that will provide beneficial effects of the drug combination. In some embodiments, "combination therapy" in defining a single composition of AAT and at least one T cell depleting agent. In some embodiments, "combination therapy" is a single composition of AAT and at least one T cell depleting agent. In some embodiments, "combination therapy" is a single kit comprising a composition comprising AAT and at least one composition comprising at least one T cell depleting agent.

In some embodiments, the T cell depleting agent and AAT are administered separately prior to transplantation. In some embodiments, the T cell depleting agent and AAT are administered concomitantly prior to transplantation. In some embodiments, the T cell depleting agent is administered prior to transplantation. In some embodiments, the T cell depleting agent is administered after transplantation. In some embodiments, AAT is administered prior to transplantation. In some embodiments, AAT is administered after transplantation. In some embodiments, the T cell depleting agent is administered prior to transplantation and after transplantation. In some embodiments, AAT is administered prior to transplantation and after transplantation.

Administration of anti-CD4 and anti-CD8 antibodies prior to transplantation results in temporal T cell depletion in said subject and, without wishing to be bound by any particular theory or mechanism of action, is coordinated with an elective transplantation session to optimally fit the absence of T cells. According to some embodiment, said anti-CD4 and anti-CD8 antibodies are administered no more than 7 days, no more than 6 days, no more than 5 days, no more than 4 days, no more than 3 days, or no more than 2 days prior to transplantation.

In another embodiment, the anti-CD4 antibody is GK1.5. In another embodiment, the anti-CD8 antibody is 53.6.72. Said antibodies are commercially available such as from BioXCell. In another embodiment, the anti-CD4 antibody exhibits similar T cell depleting activity as the GK1.5 antibody. In another embodiment, the anti-CD8 antibody exhibits similar T cell depleting activity as the 53.6.72 antibody.

T cell depleting agents are known to one skilled in the art. Non limiting examples for T cell depleting agents include anti-CD3, anti-CD4, anti-CD25, anti-CD8, anti-CD8a, anti-TCR, anti-TCR-gamma-delta and anti-thymocyte-globulin (ATG). Each possibility is a separate embodiment of the present invention.

Typically, temporary T-cell depletion relates to reduced circulating T cells for about 14 days. According to the current invention, the temporary T-cell depleting agent may be administered prior to transplantation, or in other embodiments, when the graft recipient is diagnosed as being nonresponsive to a first line of immunosuppressive treatment including but not limited to a recipient initially diagnosed as having graft dysfunction.

According to another embodiment, AAT administration is a long term administration. According to another embodiment, said AAT administration is selected from single-dose administration or sequential administration. According to another embodiment, AAT is administered prior to transplantation, following transplantation or a combination thereof. According to another embodiment, administering AAT prior to treatment is for no more than 10 days prior to transplantation.

According to another embodiment, the AAT is human AAT (hAAT). According to another embodiment, said hAAT comprises an amino acid sequence as set forth in SEQ ID NO: 1. According to another embodiment, said hAAT consists of an amino acid sequence as set forth in SEQ ID NO: 1 (MPSSVSWGILLAGLCCLVPVSLAEDPQGDAAQKT-DTSHHDQDHPTFNKITPNLAE FAFSLYRQLAHQSN-STNIFFSPVSIATAFAMLSLGTKADTHDEILEGLNFN-LTEIPEA QIHEGFQELLRTLNQPDSQLQLTTGNGL-FLSEGLKLVDKFLEDVKKLYHSEAFTVN FGDHEE-AKKQINDYVEKGTQGKIVDLVKELDRDTV-FALVNYIFFKGKWERPFEVK DTEDEDFHVDQVTTVKVPMMKRLGMFNIQHCK-KLSSWVLLMKYLGNATAIFFLP DEGKLQHLENELTH-DIITKFLENEDRRSASLHLPKLSITGTYDLKSVLGQL-GITKVF SNGADLSGVTEEAPLKLSKAVHKAVLTIDEK-GTEAAGAMFLEAIPMSIPPEVKFNK PFV-FLMIEQNTKSPLFMGKVVNPTQK).

According to another embodiment, said AAT is an analog, derivative or fragment of hAAT. According to another embodiment, said AAT is a recombinant AAT. According to another embodiment, said AAT is a plasma-derived AAT.

One of skill in the art will recognize that individual substitutions, deletions or additions to a peptide, or protein sequence (e.g., hAAT sequence) which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D). Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);

4) Arginine (R), Lysine (K);
5) Isoleucine (I), Leucine (L), Methionine (M), Valine (V); and
6) Phenylalanine (F), Tyrosine (Y), Tryptophan (W) (see, e.g., Creighton, Proteins, 1984).

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

The phrase "conservative substitution" also includes the use of a chemically derivatized residue in place of a non-derivatized residue provided that such peptide displays the requisite function of as specified herein.

The term "derived from" or "corresponding to" refers to construction of a peptide based on the knowledge of a sequence using any one of the suitable means known to one skilled in the art, e.g. chemical synthesis in accordance with standard protocols in the art. A peptide derived from hAAT can be an analog, fragment, conjugate (e.g. a lipopeptide conjugate) or derivative of a native hAAT, and salts thereof, as long as said peptide retains its ability to protect the transplant from inflammation.

Typically, the present invention encompasses derivatives of AAT. The term "derivative" or "chemical derivative" includes any chemical derivative of AAT having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a derivative can differ from the natural sequence of the peptides of the invention by chemical modifications including, but are not limited to, terminal-NH$_2$ acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The derivatives and analogs according to the principles of the present invention can also include side chain bond modifications, including but not limited to —CH$_2$—NH—, —CH$_2$—S—, —CH$_2$—S=O, O=C—NH—, —CH$_2$—O—, —CH$_2$—CH$_2$—, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C—O—O—C(R)H—N); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino is ob utyric acid, and 3-(3'-pyridyl-Ala).

Furthermore, the analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (MeAla), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

Pharmaceutical Compositions The pharmaceutical compositions of the invention can be formulated in the form of a pharmaceutically acceptable salt of the peptides of the present invention or their analogs or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously.

Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences by E. W. Martin, the contents of which are hereby incorporated by reference herein.

The therapeutically effective amount of the components of the present invention (e.g., AAT and anti-CD4/CD8 antibodies), which will be effective in the prevention and treatment of graft rejection can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Toxicity and therapeutic efficacy of the compositions described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

Depending on the location of the tissue of interest, the compositions of the present invention can be supplied in any manner suitable for the provision of the peptide to cells within the tissue of interest. Thus, for example, a composition of the present invention can be introduced, for example, into the systemic circulation, which will distribute the peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

Suitable routes of administration include, but are not limited to, parenteral injections, e.g., intradermal, intravenous, intramuscular, intralesional, subcutaneous, intrathecal, and any other mode of injection as known in the art. Although the bioavailability of polypeptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material. According to some preferred embodiments, administration can be by direct injection e.g., via a syringe, at the site of a damaged tissue.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as a fatty oil. In addition, dosage unit forms can contain various other materials which modify the physical form of the dosage unit, for example, coatings of sugar, shellac, or other enteric agents. The tablets of the invention can further be film coated.

EXAMPLES

Animals. hAAT lung-specific transgenic mice (C57BL/6 background) were a kind gift from Prof. A. Churg (University of British Columbia, Vancouver, Canada). Six-to-eight-week old heterozygote siblings from breeding couples of WT C57BL/6 (Harlan laboratories Inc., Israel)×human AAT lung-specific transgenic mice were used as graft recipients, as described elsewhere (19). Nine-to-ten-week old Sprague Dawley female rats (Harlan laboratories) were used as pancreatic islet and skin donors. Experiments were approved by institutional Animal Care and Use Committee.

Pancreatic islet isolation. Donor rats were anesthetized and then bled. The bile duct was ligated at the liver and at the intestinal ends, then cannulated with a 27G needle. The pancreas was inflated with 10 ml cold collagenase (1 mg/ml, type XI, Sigma, Israel), removed and incubated for 17 minutes at 37° C. while continuously stirred with a 3 mm sterile magnet. Digested pancreas was mechanically sheared by vortex and tissue was filtered through a 1,000 µm sieve.

Islets were collected from a double-Ficoll gradient (1.0771 and 1.1191, Sigma). The resulting material was washed in Hanks balanced salt solution (HBSS) containing 0.5% bovine serum albumin (BSA) (cell-culture tested, Sigma), centrifuged at 900 revolutions per minute (rpm) and then reconstituted in culture medium containing RPMI-1640, 10% fetal calf serum (FCS) (both from Biological Industries, Beit Haemek, Israel), 50 units/ml penicillin and 50 µg/ml streptomycin (both from Cellgro, Mediatech, Herndon, Va., USA). Pancreatic islets were then hand-picked under a stereoscope into a culture flask and incubated overnight.

Islet xenotransplantation. Islet transplantation in the renal subcapsular space was performed as described, with minor modifications (19). Rat islets (315-400/transplant) were implanted under the renal capsule of recipient mice that were rendered hyperglycemic by single-dose streptozotocin (225 mg/kg, Sigma). A relatively small number of xenogeneic islets (315-400) were implanted. Prospective recipients were screened for non-fasting circulating glucose levels of ~400 mg/dl. Blood glucose was followed three times a week, and graft failure was determined by glucose values exceeding 300 mg/dl after at least three days of normoglycemia.

Skin xenotransplantation. Skin transplantation was performed as described (19) with minor modifications. Donor rats were anesthetized, abdominal midline was shaved and excised skin was placed in cold phosphate-buffered saline (PBS). Blood vessels and hypodermis were removed using sterile blade and the skin was cut into 1 mm² pieces under a stereoscope. Grafts were implanted subcutaneously in the inner-thigh region of recipients and incision sites were stitched closed.

Treatment protocols. hAAT (Aralast™, Baxter, Westlake Village, Calif., USA) was introduced at 60 and 240 mg/kg, intraperitoneally (i.p.) and at either 1 or 10 days prior to transplantation. Therapy continued every 3 days throughout the experiments, as described (19). The maximal treatment duration was 80 days. Temporary T cell depletion (also termed debulking therapy) included a single dose of a mixture of depleting polyclonal anti-CD4 (GK1.5) and anti-CD8 (53.6.72) antibodies (BioXCell), each at 300 µl at the concentration of 1 mg/ml, 3 days prior to transplantation. Subtherapeutic co-stimulation blockade included an equal mixture of anti-LFA-1 and anti-CD154 monoclonal antibodies (MR-1 and FD441.8, respectively, BioXCell, West Lebanon, N.H., USA), each at 25 µl/injection at the concentration of 1.25 mg/ml, one day before transplantation and every three days thereafter. The maximal treatment duration was 40 days.

Histology and immunohistochemistry. Explanted kidneys carrying implants were fixed in 10% formalin (Sigma) for 24 h and transferred into 70% ethanol. The specimens were cut through the center of the implant, embedded in paraffin and sectioned. For histological examination, Hematoxylin and Eosin (H&E) was performed. Insulin immunostaining was performed with guinea-pig-anti-swine-insulin, detected by Cy3-donkey-anti-guinea-pig (both 1:200, DakoCytomation, Glostrup, DK); B cell immunostaining was performed with rat-anti-mouse-B220 (1:100, eBioscience, San-Diego, Calif., USA), detected by DyLight488-goat-anti-rat (1:200, Jackson IR, PA, USA); T cell immunostaining was performed with Armenian-hamster-anti-CD3 (BioLegend, San-Diego, Calif., USA), detected by fluorescence isothiocyanate (FITC)-rat-anti-Armenian-hamster (eBioscience), both at 1:50; Treg immunostaining was performed with mouse-anti-mouse-foxp3 (Biolegend), detected by Cy2-donkey-anti-mouse (Jackson IR), both at 1:100. Nuclei were depicted by 4',6-diamidino-2-phenylindole (DAPI) staining (1 g/ml, Sigma). Immunofluorescence was detected using Olympus BX60 (Olympus UK Ltd., London, UK).

Reverse transcriptase-polymerase chain reaction (RT-PCR). Total RNA was extracted from DLN or implants using RNA extraction kit (5Prime PerfectPure RNA Tissue Kit, MD, USA). Reverse transcription was performed using Verso complementary DNA (cDNA) Kit (Thermo scientific UK). cDNA amplification was undertaken by PCR (XP Cycler, BIOER) set at 28-43 cycles, depending on gene expression intensity. The results were collected from a series of at least 3 different cycles, normalized to β-actin and calculated as fold from control.

TABLE 1

Species-specific primers used for RT-PCR

| Specie | Gene | Forward primer '5 to 3' | Reverse primer '5 to 3' |
|---|---|---|---|
| Mouse | β-actin | GGGTCAGAAGGATTCCTATG (SEQ ID NO: 2) | GGTCTCAAACATGATCTGGG (SEQ ID NO: 3) |
| | CD3 | GCCTCAGAAGCATGATAAGC (SEQ ID NO: 4) | CCCAGAGTGATACAGATGTC (SEQ ID NO: 5) |
| | CD14 | GCCTCAGAAGCATGATAAGC (SEQ ID NO: 6) | CCCAGAGTGATACAGATGTC (SEQ ID NO: 7) |
| | IL-1β | CTCCATGAGCTTTGTACAAGG (SEQ ID NO: 8) | TGCTGATGTACCAGTTGGGG (SEQ ID NO: 9) |
| | CD86 | TCCAGAACTTACGGAAGCACCCACG (SEQ ID NO: 10) | CAGGTTCACTGAAGTTGGCGATCAC (SEQ ID NO: 11) |
| | CD40 | ATTTGTGCCAGCCAGGAAGCCG (SEQ ID NO: 12) | GCATCCGGGACTTTAAACCACAGA (SEQ ID NO: 13) |
| | IL-6 | CTGGGAAATCGTGGAAATGAG (SEQ ID NO: 14) | GTTAGGAGAGCATTGGAAATTGG (SEQ ID NO: 15) |
| | 1L-10 | AGGACTTTAAGAGTTACTTGG (SEQ ID NO: 16) | CTATGCAGTTGATGAAGATGTC (SEQ ID NO: 17) |
| | B220 | CCTTTGTGATGAGTTACTGGA (SEQ ID NO: 18) | CCTTCCTCTTGGAATGTCTC (SEQ ID NO: 19) |
| | LY94 | GTCACAAATGGAAACTCGGT (SEQ ID NO: 20) | TCATACAGACCACTTACTACCAG (SEQ ID NO: 21) |

TABLE 1-continued

Species-specific primers used for RT-PCR

| Specie | Gene | Forward primer '5 to 3' | Reverse primer '5 to 3' |
|---|---|---|---|
| Rat | β-actin | GGCTTTAGGAGCTTGACAATACTG (SEQ ID NO: 22) | GCATTGGTCACCTTTAGATGGA (SEQ ID NO: 23) |
| | insulin | GCAAGCAGGTCATTGTTCC (SEQ ID NO: 24) | TGCCAAGGTCTGAAGATCC (SEQ ID NO: 25) |
| | MCP-1 | CTGCTGCTACTCATTCACTG (SEQ ID NO: 26) | CTTGGTGACAAATACTACAGCT (SEQ ID NO: 27) |

In vitro islet stimulation. Rat pancreatic islets (50/well in 48-well plates in triplicate) were cultured with medium alone or with recombinant IL-1β (10 ng/ml, R&D Systems), in the presence or absence of a 1 h pretreatment with hAAT (0.5 mg/ml). Nitrite concentration was determined after 72 h by Griess assay (Promega, Wis., USA).

FACS analysis. Percent CD3+ cells out of circulating CD45+ leukocytes was determined in fresh heparinized whole blood obtained from mouse-tails. Red blood cells (RBC) were lysed using RBC lysis buffer followed by double-staining with FITC-anti-CD3 (BD Biosciences) and APC-anti-CD45 (eBioscience). Each sample contained at least 1×106 cells. Percent B cells in DNL were determined in single-cell suspensions of excised lymph nodes. Triple-staining was preformed using phycoerythrin (PE)-anti-CD40, FITC-anti-CD19 and APC-anti-B220 antibodies (all from eBioscience and diluted according to manufacture's recommendation). FACS analysis was carried out using FACS Calibuer (Becton Dickinson). Data was analyzed using CellQuest software.

Statistical analysis. GraphPad Prism 5 (Pugh computers, UK) was used for computerized statistical analysis. Results are expressed as the mean±standard error of the mean (SEM). Significance of differences between groups was determined by two-tailed student t-test at 95% confidence interval. Survival was analyzed by Kaplan-Maier analysis. Means were considered statistically different at $p<0.05$.

Example 1 hAAT Monotherapy During Rat-to-mouse Islet Transplantation

The initial dose for hAAT monotherapy (60 mg/kg from 1 day prior to transplantation) was selected from previous reports. In order to explore a higher impact monotherapy protocol, both a higher dose was examined (240 mg/kg) and an extended 10-day pretreatment protocol was tested. hAAT injections were repeated every 3 days in all experiments. A total of n (number in group)=6 mice were grafted under these conditions, including two recipients per modified protocol. In addition, n=6 mice were grafted with no added therapy, as control. As shown in FIG. 1A, neither of the three modified hAAT monotherapy protocols delayed islet xenograft rejection day (CT 10, 11, 12, 13, 15, 22 and hAAT 11, 12, 13, 14, 15, 24). The extended hAAT protocol is thereby used throughout the following studies.

Intragraft changes were examined (FIG. 1B-D). According to histology on day 7 post-transplantation (n=3 per group, representative images), infiltrate and various degrees of islet remains appeared similar between groups (FIG. 1B). Rat and mouse gene expression levels were examined on days 3 and 7 post-transplantation (n=3 for each group and time-point). The expression of mouse IL-1β significantly decreased 20-fold on average in the hAAT-treated group. Mouse CD14 decreased by 1.72 on average, as did infiltrating CD3 and B220 transcripts. Rat MCP-1 decreased by 1.74 on average and insulin transcript levels increased 2.1-fold (FIG. 1C-D). No significant differences were observed in the expression of mouse LY94, a natural killer (NK) cell marker (not shown). According to insulin immunohistochemistry of grafts from 3 days post-transplantation (not shown), islets appeared partially damaged morphologically and nuclear staining revealed infiltration of cells around islets in both groups.

Rat islets responded to hAAT in a comparable manner to mouse islets (23); hAAT (0.5 mg/ml) decreased IL-1β-stimulated nitric oxide release by 30% (not shown).

Example 2

DLN Molecular Profile During hAAT Monotherapy

Figure 2:
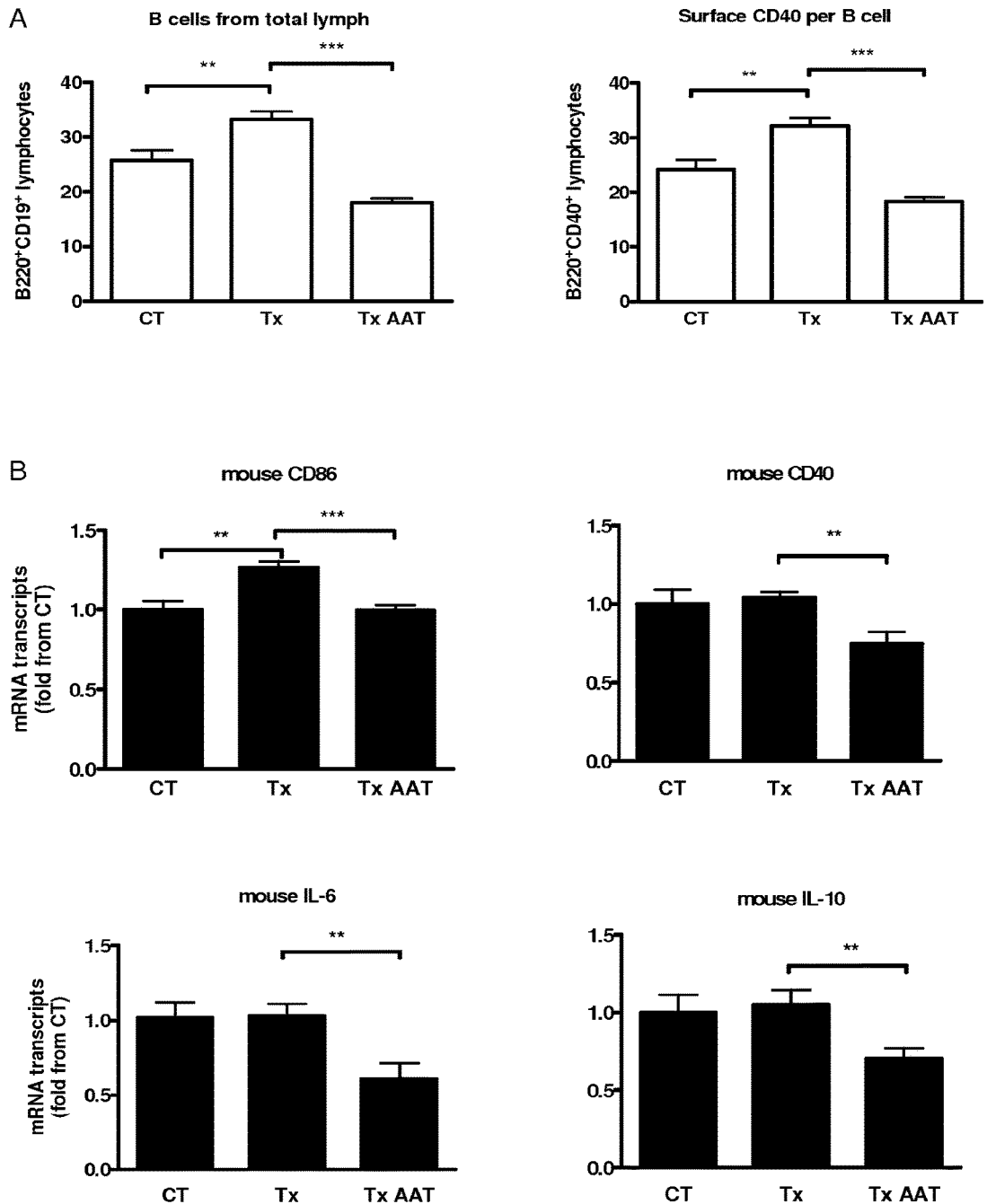
FIG. 2 is a graphic illustration of draining lymph nodes (DLN) response to human AAT monotherapy after skin xenografting. Mice were either SHAM operated (CT) or recipients of rat skin (Tx) in the absence or presence of human AAT monotherapy. (A) 14-day DLN. FACS analysis. Results expressed as fold change from CT, mean±SEM from n=10/group; $p<0.01$, *$p<0.001$. (B) 72-h DLN. RT-PCR. Results expressed as fold change from CT, mean±SEM from n=3/group; $p<0.01$, *$p<0.001$.
Figure 4:
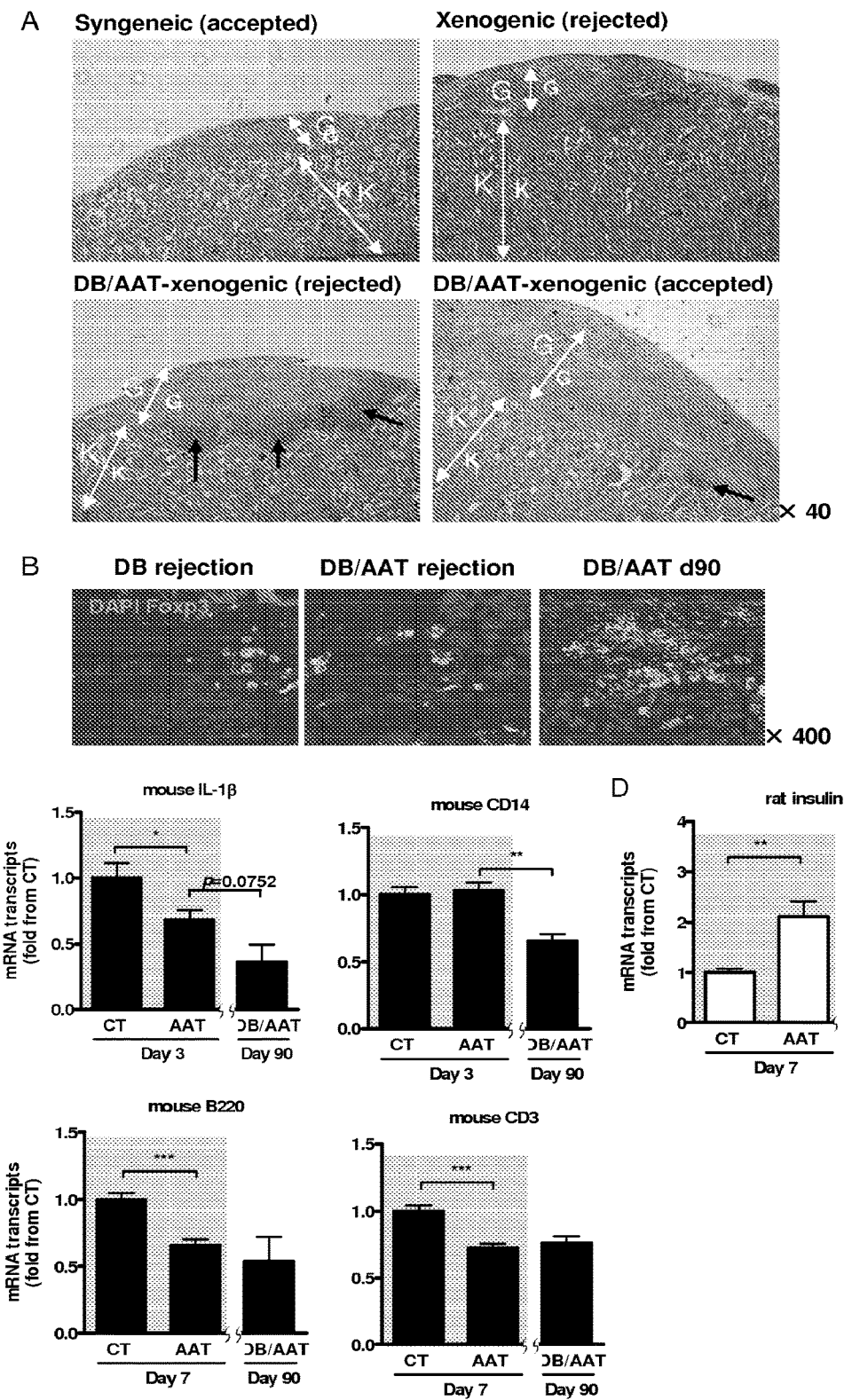
FIG. 4 illustrates AAT treatment combined with debulking therapy; histology and gene expression. Rat islets were grafted into mice that were treated with anti-CD4/CD8 depleting antibodies, in the absence of AAT therapy (n=7) or with added AAT therapy (n=5), as in FIG. 3B. (A) Graft site histology. K, kidney tissue; G, graft site. From left to right, representative syngeneic mouse islet graft (day 35), xenograft (debulking therapy alone, day 25), black arrows indicate immune cell mononuclear infiltration, xenograft (debulking therapy combined with AAT, day 11 after rejection) and xenograft (debulking therapy combined with AAT, day 90). (B) Treg cell content in xenograft sites. Immunofluorescent staining. DB, debulking therapy alone (rejected graft); DB/AAT, combined debulking and AAT therapy (rejected and accepted grafts). Green, foxp3; blue, DAPI nuclear counterstaining. Representative images. (C) Mouse (recipient) gene expression profiles. RT-PCR. CT vs. AAT monotherapy on day 7 shown over gray background, next to day 90 explants from mice treated by the combination of debulking therapy and AAT (DB/AAT). Results expressed as fold change from CT, mean±SEM from n=3/group; *$p<0.05$, $p<0.01$, *$p<0.001$. (D) Rat (donor) insulin expression profile. RT-PCR. CT vs. AAT monotherapy, see

In order to achieve a robust immune response, improve detection of changes in DLN, and achieve responses with low variability, skin xenotransplantation was performed. Treatment groups included control mice and mice receiving hAAT. Day-14 inguinal DLN were collected for FACS analysis. As shown in FIG. 2A, the number of B cells in the lymph nodes rose by 22.4% on average in transplanted mice, compared to control non-grafted mice. However, hAAT-treated mice displayed a 54.2% decrease on average of B cells from skin transplanted untreated mice. Surface levels of CD40 significantly increased compared to non-grafted mice, and then reduced with hAAT treatment (FIG. 2A).

DLN RT-PCR analysis was performed 3 days after transplantation. FIG. 2B depicts relative changes in specific transcript numbers. While DLN CD40, IL-6 and IL-10 transcript levels did not increase after xenotransplantation at this time point, CD86 displayed a significant increase from non-grafted mice. In the presence of systemic hAAT, CD40 was reduced by 28.3% on average, CD86 by 21.5%, IL-6 by 40.6% and IL-10 by 32.87% (FIG. 2B).

Example 3

Islet Xenotransplant Survival is Extended under hAAT and Temporary T Cell Depletion Combination Since monotherapy with hAAT appears to have allowed an uninterrupted xeno-response, we sought to examine the combination of hAAT treatment with a technique for modifying xenoimmunity, namely, temporary T cell depletion.

Debulking therapy was examined alone and in combination with hAAT (FIG. 3A-E and FIG. 4). Recipient mice were treated with single-dose anti-CD8/CD4 depleting antibodies, with or without hAAT (n=5-7 per group). According to circulating mouse CD45+CD3+ follow-up (FIG. 3A, representative result), mice injected with depleting antibodies exhibited a decrease in the relative number of circulating T cells and a spontaneous return to normal lymphocyte levels after a period of approximately two weeks.

As shown in FIG. 3B, animals treated by debulking therapy (DB) displayed a delay in xenograft rejection (days 28, 31, 31, 33, 33, 40, 52). In contrast, combined debulking therapy with hAAT (DB/AAT) resulted in islet xenograft surviving until days 59, 61, >90, >90, >90. In addition, a group of animals was examined for the outcome of combined debulking therapy with 60 mg/kg hAAT (n=6, not shown). Three out of 6 recipients displayed rejection days at the range of debulking therapy alone (22, 29, 32, 74, 83, >84). Furthermore, a larger percentage of mice (from day 15 onwards) exhibited functional islet xenografts when treated with either a combination of AAT/anti-CD4 or AAT/anti-CD8 (compared to a monotherapy with each of the antibodies or AAT).

In order to assess whether combined debulking therapy and hAAT promotes strain-specific immune tolerance, islet grafts were recovered from long-lasting recipients (n=3), and mice were allowed to return to hyperglycemic values. A second graft of rat islets was placed under the right renal capsule. As shown in FIG. 3C (representative glucose follow-up), acute rejection was observed.

Example 4 hAAT and Temporary T Cell Depletion Combination Results in Modified Graft Site Immune Infiltration and Gene Expression Profiles In allogeneic islet transplant model (Lewis el al. Proc Natl Acad Sci USA 2008;105(42):16236-16241), hAAT monotherapy resulted in a non-invasive population of mononuclear cells that was located in the region between the renal tissue, capsule and graft, containing Tregs. Here, the histological images of islet grafts that lack an immune infiltrate (syngeneic mouse islet transplants) was compared with histological samples collected from untreated xenogenic grafts, as well as xenogenic transplants treated by combination of debulking therapy and hAAT that were either accepted or rejected. As shown in FIG. 4A (representative histological images), 35-day syngeneic islet graft sites are characterized by lack of an immune infiltrate and untreated xenotransplants displayed robust infiltration throughout the graft site (shown, 10 days after rejection). Histology obtained from treated mice was divided into two: shown, a graft that was rejected on day 59 and examined 11 days later, and a graft that was accepted (obtained 90 days post-transplantation). As shown, the rejected graft presented with a marginal mononuclear cell infiltrate that was not limited to the region between capsule, graft and kidney, but rather appeared to line the border with the host (black arrows). In contrast, accepted xenograft displayed a restricted infiltrate adjacent to the capsule and consistent with that found in long-term allogeneic hAAT-treated islet transplants.

Example 5 hAAT and Temporary T Cell Depletion Combination Decreases T and B Lymphocyte Content in Xenografts and Promotes Local foxp3+ Tregs Explanted grafts were analyzed for T and B cell markers, as well as for Tregs immunohistochemistry. As shown in FIG. 4B, representative images from grafts: debulking therapy 10 days after rejection, DB/AAT 11 days after rejection and DB/AAT that did not reject. Foxp3-positive Tregs were abundant in the accepted grafts. In addition, populations of CD3+ and B220+ cells were reduced in both debulking alone and combined debulking and hAAT, compared to untreated animals (not shown).

Example 6 hAAT and Temporary T Cell Depletion Combination Affects Intragraft Gene Expression Profile Since the majority of grafts treated solely by T cell debulking did not survive beyond day 30, gene expression was examined between samples from day-7 untreated (CT) or hAAT-treated (AAT) xenografts (shaded gray) and day-90 combination therapy (DB/AAT) (FIG. 4C). CD3 and B220 results are also shown in FIG. 1C, repeated here to facilitate visual comparison. As shown, combined treatment with hAAT and temporary T cell depletion reduced mouse gene transcripts of IL-1$\beta$ and CD14 (a decrease of 47.15% and 36.16% on average, respectively) in comparison to hAAT monotreatment on day-7. However, no significant difference was observed in the number of CD3 and B220 transcripts between both hAAT-treated groups. Rat insulin transcripts were greater in day-90 combined-therapy compared to both day-7 groups (FIG. 4D).

Example 7

Islet Xenotransplants are Rejected under hAAT and Low-Dose Co-Stimulation bblockade Combination Since combined treatment of hAAT and depleting antibodies resulted in extension of xenograft survival, hAAT with a combination of co-stimulation blockade was examined as another way for a possible xenograft survival. Mouse monoclonal anti-CD154 and anti-LFA-1 antibodies promote xenograft survival (Arefanian et al., Cell Transplant 2007; 16(8):787-798; Arefanian et al., Diabetes 2010; 59(4):958-966). Recipients were treated with low-dose co-stimulation blockade with or without hAAT (n=6 per group). Treatment with low-dose co-stimulation blockade alone displayed a rejection rate similar to that of control untreated recipient mice (median day of rejection 12.5). Similarly, combination of low-dose co-stimulation blockade and hAAT resulted in a non-significant change to outcomes of control or low-dose co-stimulation blockade alone; the grafts were rejected on days overlapping the control group.

Figure 5:
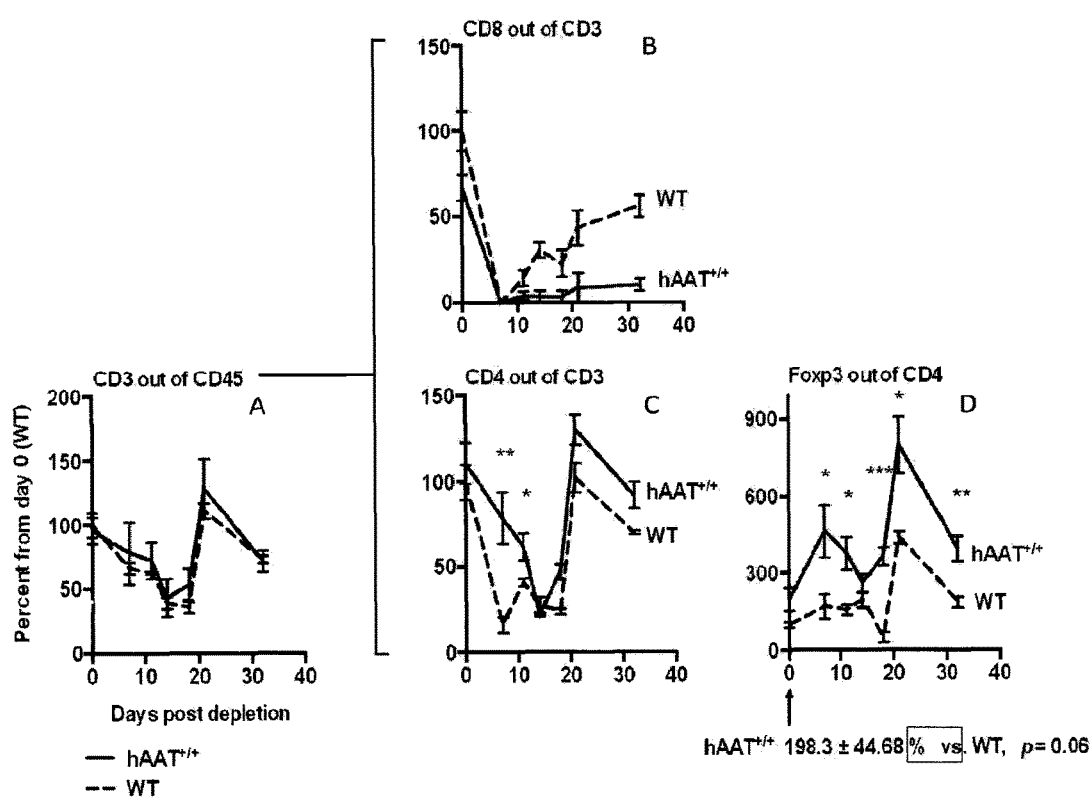
FIG. 5 are graphs showing that hAAT promotes expansion of foxp3 positive CD4 T-cells and delays CD8 T-cell repopulation after T-cell depletion. C57BL/6 (WT) and hAAT transgenic mice (hAAT$^{+/+}$) n=5 per group underwent systemic T-cell depletion using the combination of anti-CD4 and anti-CD8 depleting antibodies. (A) shows the interplay between CD3 and CD45 expression; (B) shows the interplay between CD8 and CD3 expression; (C) shows the interplay between CD4 and CD3 expression; (B) shows the interplay between F0xp3 and CD4 expression. Subpopulation follow-up in peripheral blood. Mean±SEM; *$p<0.05$, **$p<0.01$, $p<0.001$.

In an experiment, wherein C57BL/6 (WT) and hAAT transgenic mice were used to determine the impact of hAAT in altering the abundance of foxp3 positive CD4 T-cells and CD8 T-cell re-population after T-cell depletion, it was found that hAAT promotes expansion of foxp3 positive CD4 T-cells and delays CD8 T-cell re-population after T-cell depletion (FIG. 5).

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

The invention claimed is:

1. A method of preventing or treating xenotransplant rejection in a subject in need thereof, the method comprising administering to the subject prior to transplantation of said xenotransplant a therapeutically effective amount of alpha-1-antitrypsin (AAT) in combination with a therapeutically effective amount of an anti-CD8 antibody or an antigen binding fragment thereof, thereby preventing or treating xenotransplant rejection in the subject.

2. The method of claim 1, further comprising administering anti-CD4 antibody or an antigen binding fragment thereof.

3. The method of claim 1, wherein said administering is administering no more than 14 days prior to said transplantation.

4. The method of claim 1, wherein administering of: (1) said AAT and (2) said anti-CD8 antibody or said antigen binding fragment thereof is concomitantly administrated.

5. The method of claim 1, wherein said AAT comprises an amino acid sequence as set forth in SEQ ID NO: 1.

6. The method of claim 1, wherein said AAT is a recombinant protein.

7. The method of claim 1, wherein said AAT is further administered following transplantation.

8. The method of claim 1, wherein the subject is a human.

9. The method of claim 1, wherein said xenotransplant is selected from the group consisting: cells, pancreatic islets, pancreas, heart, lung, kidney, liver or skin.

10. The method of claim 1, wherein said subject is afflicted with graft dysfunction or at risk of acquiring graft dysfunction.

11. A method of preventing or treating xenotransplant rejection in a subject in need thereof, the method comprising administering to the subject prior to transplantation of said xenotransplant a therapeutically effective amount of alpha-1-antitrypsin (AAT) in combination with a therapeutically effective amount of at least one temporary T cell depleting agent, thereby preventing or treating xenotransplant rejection in the subject.

12. The method of claim 11, wherein the at least one temporary T cell depleting agent is selected from the group consisting: an anti-CD4 antibody, anti-CD8 antibody, an antigen binding fragments of anti-CD4, an antigen binding fragments of anti-CD8, or any combination thereof.

* * * * *

SEQUENCE LISTING

<160> NUMBER OF SEQ ID NOS: 27

<210> SEQ ID NO 1
<211> LENGTH: 417
<212> TYPE: PRT
<213> ORGANISM: homo sapiens

<400> SEQUENCE: 1

```
Met Pro Ser Ser Val Ser Trp Gly Ile Leu Leu Ala Gly Leu Cys Cys
1               5                   10                  15

Leu Val Pro Val Ser Leu Ala Glu Asp Pro Gln Gly Asp Ala Ala Gln
            20                  25                  30

Lys Thr Asp Thr Ser His His Asp Gln Asp His Pro Thr Phe Asn Lys
        35                  40                  45

Ile Thr Pro Asn Leu Ala Glu Phe Ala Phe Ser Leu Tyr Arg Gln Leu
    50                  55                  60

Ala His Gln Ser Asn Ser Thr Asn Ile Phe Phe Ser Pro Val Ser Ile
65                  70                  75                  80

Ala Thr Ala Phe Ala Met Leu Ser Leu Gly Thr Lys Ala Asp Thr His
                85                  90                  95

Asp Glu Ile Leu Glu Gly Leu Asn Phe Asn Leu Thr Glu Ile Pro Glu
            100                 105                 110

Ala Gln Ile His Glu Gly Phe Gln Glu Leu Leu Arg Thr Leu Asn Gln
        115                 120                 125

Pro Asp Ser Gln Leu Gln Leu Thr Thr Gly Asn Gly Leu Phe Leu Ser
    130                 135                 140

Glu Gly Leu Lys Leu Val Asp Lys Phe Leu Glu Asp Val Lys Lys Leu
145                 150                 155                 160

Tyr His Ser Glu Ala Phe Thr Val Asn Phe Gly Asp His Glu Glu Ala
                165                 170                 175

Lys Lys Gln Ile Asn Asp Tyr Val Glu Lys Gly Thr Gln Gly Lys Ile
            180                 185                 190

Val Asp Leu Val Lys Glu Leu Asp Arg Asp Thr Val Phe Ala Leu Val
        195                 200                 205

Asn Tyr Ile Phe Phe Lys Gly Lys Trp Glu Arg Pro Phe Glu Val Lys
    210                 215                 220

Asp Thr Glu Asp Glu Asp Phe His Val Asp Gln Val Thr Thr Val Lys
225                 230                 235                 240

Val Pro Met Met Lys Arg Leu Gly Met Phe Asn Ile Gln His Cys Lys
                245                 250                 255

Lys Leu Ser Ser Trp Val Leu Leu Met Lys Tyr Leu Gly Asn Ala Thr
            260                 265                 270

Ala Ile Phe Phe Leu Pro Asp Glu Gly Lys Leu Gln His Leu Glu Asn
        275                 280                 285

Glu Leu Thr His Asp Ile Ile Thr Lys Phe Leu Glu Asn Glu Asp Arg
    290                 295                 300

Arg Ser Ala Ser Leu His Leu Pro Lys Leu Ser Ile Thr Gly Thr Tyr
305                 310                 315                 320

Asp Leu Lys Ser Val Leu Gly Gln Leu Gly Ile Thr Lys Val Phe Ser
                325                 330                 335

Asn Gly Ala Asp Leu Ser Gly Val Thr Glu Glu Ala Pro Leu Lys Leu
            340                 345                 350

Ser Lys Ala Val His Lys Ala Val Leu Thr Ile Asp Glu Lys Gly Thr
        355                 360                 365
```

-continued

Glu Ala Ala Gly Ala Met Phe Leu Glu Ala Ile Pro Met Ser Ile Pro
370                 375                 380

Pro Glu Val Lys Phe Asn Lys Pro Phe Val Phe Leu Met Ile Glu Gln
385                 390                 395                 400

Asn Thr Lys Ser Pro Leu Phe Met Gly Lys Val Val Asn Pro Thr Gln
            405                 410                 415

Lys

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gggtcagaag gattcctatg                                                20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggtctcaaac atgatctggg                                                20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcctcagaag catgataagc                                                20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cccagagtga tacagatgtc                                                20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gcctcagaag catgataagc                                                20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cccagagtga tacagatgtc                                              20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ctccatgagc tttgtacaag g                                            21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgctgatgta ccagttgggg                                              20

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
tccagaactt acggaagcac ccacg                                        25

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
caggttcact gaagttggcg atcac                                        25

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
atttgtgcca gccaggaagc cg                                           22

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gcatccggga ctttaaacca caga                                         24

<210> SEQ ID NO 14
<211> LENGTH: 21

<212> TYPE: DNA
<213> ORGANISM: Artificial Sequence
<220> FEATURE:
<223> OTHER INFORMATION: primer

<400> SEQUENCE: 14
ctgggaaatc gtggaaatga g                                            21

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
gttaggagag cattggaaat tgg                                          23

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
aggactttaa gggttacttg g                                            21

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
ctatgcagtt gatgaagatg tc                                           22

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
cctttgtgat gagttactgg a                                            21

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ccttcctctt ggaatgtctc                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
gtcacaaatg gaaactcggt                                          20

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
tcatacagac cagttactac cag                                      23

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
ggctttagga gcttgacaat actg                                     24

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
gcattggtca cctttagatg ga                                       22

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
gcaagcaggt cattgttcc                                           19

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
tgccaaggtc tgaagatcc                                           19

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ctgctgctac tcattcactg                                          20

<210> SEQ ID NO 27
<211> LENGTH: 22
<212> TYPE: DNA
<213> ORGANISM: Artificial Sequence

```
<220> FEATURE:
<223> OTHER INFORMATION: primer

<400> SEQUENCE: 27
cttggtgaca aatactacag ct                                                    22
```